United States Patent [19]

Klawitter

[11] 4,326,304
[45] Apr. 27, 1982

[54] HEART VALVE WITH PIVOTED OCCLUDER

[75] Inventor: Jerome J. Klawitter, New Orleans, La.

[73] Assignee: Hemex, Inc., Austin, Tex.

[21] Appl. No.: 182,869

[22] Filed: Sep. 17, 1980

[51] Int. Cl.³ ............................................. A61F 1/22
[52] U.S. Cl. .................................. 3/1.5; 137/527.8
[58] Field of Search ................... 3/1.5; 137/527, 527.8

[56] References Cited

U.S. PATENT DOCUMENTS

| 3,448,465 | 6/1929 | Pierce et al. | 3/1.5 |
| 3,546,711 | 12/1970 | Bokros | 3/1.5 |
| 3,825,957 | 7/1974 | Kaster | 3/1.5 |
| 3,835,475 | 9/1974 | Child | 3/1.5 |
| 3,859,668 | 1/1975 | Anderson | 3/1.5 |
| 3,926,215 | 12/1975 | Macleod | 3/1.5 X |
| 4,225,980 | 10/1980 | Martinez | 3/1.5 |
| 4,240,161 | 12/1980 | Huffstutler, Jr. et al. | 3/1.5 |
| 4,254,508 | 3/1981 | Bokros | 3/1.5 |

FOREIGN PATENT DOCUMENTS 2753159  5/1979  Fed. Rep. of Germany .

Primary Examiner—Ronald L. Frinks
Attorney, Agent, or Firm—Fitch, Even, Tabin, Flannery & Welsh

[57] ABSTRACT

A heart valve has an elliptical occluder mounted for pivoting in an annular heart valve body with a circular passageway between an open position to allow blood flow through the passageway and a closed position to block blood flow. A pair of ears extend from the occluder into a pair of opposed pie-shaped depressions in the interior wall of the valve body so that the relative rotation of the ears along the verticies of the depressions defines an eccentric pivot axis. The occluder seats in its closed position against a lip which protrudes inward of the interior wall on the major side of the eccentric axis.

7 Claims, 6 Drawing Figures

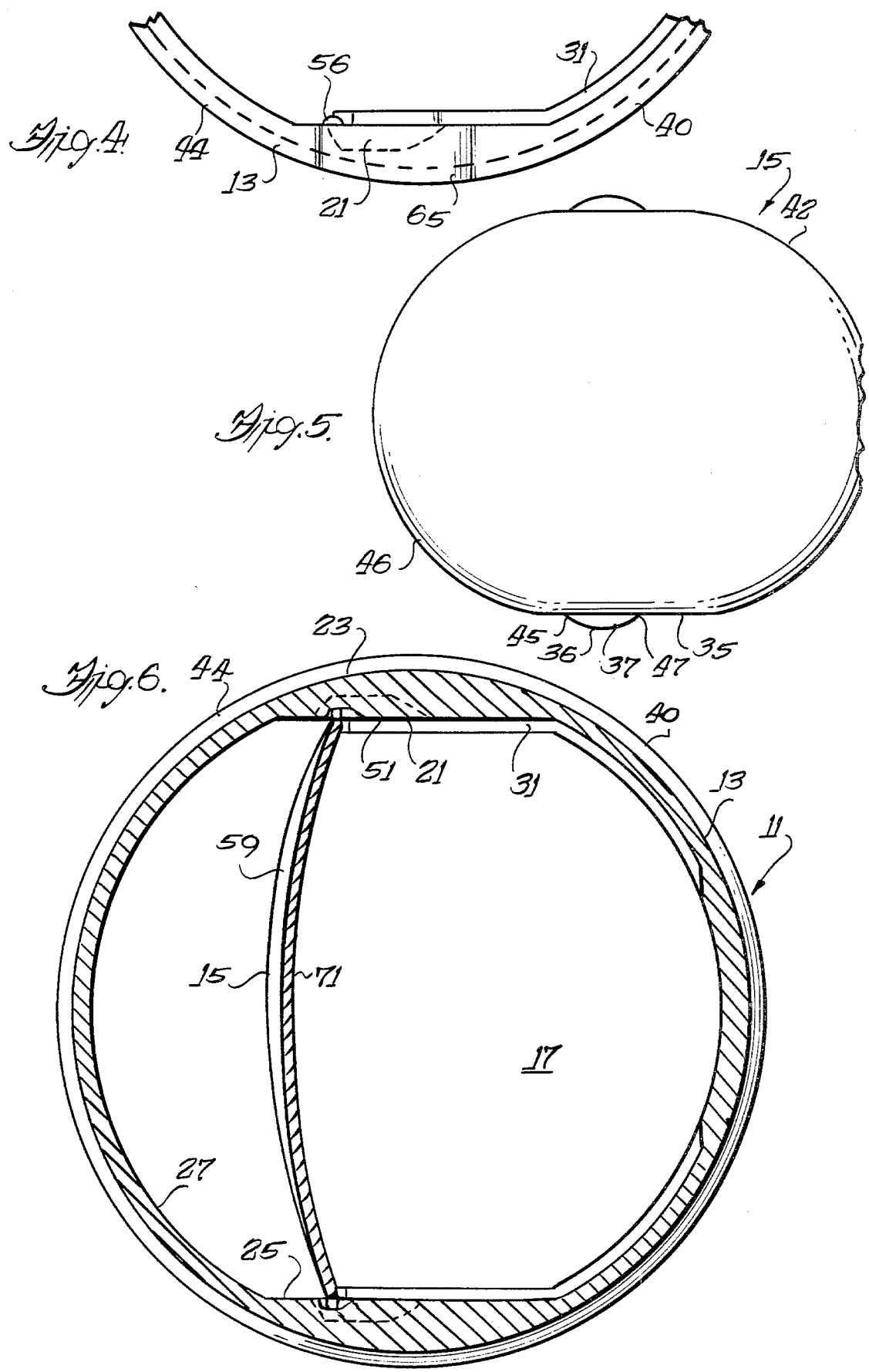

HEART VALVE WITH PIVOTED OCCLUDER

BACKGROUND OF THE INVENTION

This invention relates to heart valve prostheses for replacement of defective natural valves and more particularly to heart valve prostheses using a pivoting valve member.

Early designs of disc-shaped occluder heart valves, such as that described in U.S. Pat. No. 3,448,465, employ eccentric pivots by which the disc-shaped occluders pivot between an open position to allow blood flow through an annular passageway and a closed position in which blood flow through the passageway is blocked. In pivoting occluder heart valves, blood may tend to stagnate and clot around the pivots causing sticking of the valves. Furthermore, the continuous opening and closing of such a valve subject the pivots to continual wear which may limit the life of the heart valve.

In attempts to avoid potential problems associated with pivoting occluder valves, heart valves have been developed which have free-floating occluders. In U.S. Pat. No. 3,825,957, such an occluder has a central opening which follows a guide rod extending from the annular body of the valve, and in U.S. Pat. No. 3,835,475, a free-floating occluder is retained between upper and lower protrusions which extend from the annular body generally into the region of the passageway through the valve body. A limitation of such free-floating occluder heart valves is that the intrusions into the path of blood flow, which are necessary to retain the free-floating occluder, interfere with the smooth flow of blood through the valve.

The need continues for improved heart valve designs which will provide long-term trouble-free use, which respond quickly to pressure changes within the heart and which provide good blood flow by minimizing impediments in the blood flow path.

It is a primary object of the present invention to provide a pivoting occluder heart valve which has generally unobstructed blood flow, and which substantially eliminates problems due to pivot wear and blood stagnation at the pivots.

SUMMARY OF THE INVENTION

The invention provides a heart valve prosthesis having a generally circular passageway and an elliptical occluder or valve member which pivots between an open position which allows blood flow therethrough and a closed position which blocks blood flow therethrough. A pair of opposed pie-shaped depressions are provided in the interior wall of the valve body, and a pair of ears project from the occluder and into the depressions where the ears rotate relative to the vertices of the depressions to define an eccentric pivot axis that divides the occluder and valve body into major and minor portions. The occluder seats in its closed position along a lip which extends inward of the interior wall of the major portion of the body. The upstream edges of the depressions are spaced slightly upstream of the occluder in its closed position thereby unloading the ears and the depressions of the closing force of the occluder.

Other advantages and objects of the invention will become apparant from the following detailed description taken in conjunction with the accompanying drawings in which:

BRIEF DESCRIPTION OF THE DRAWINGS

FIG. 4 is a partial plan view of the valve body.

FIG. 5 is a plan view of the occluder.

FIG. 6 is a cross-sectional view of the valve taken along line 6—6 of FIG. 2.

DETAILED DESCRIPTION OF THE PREFERRED EMBODIMENT

Figure 1:
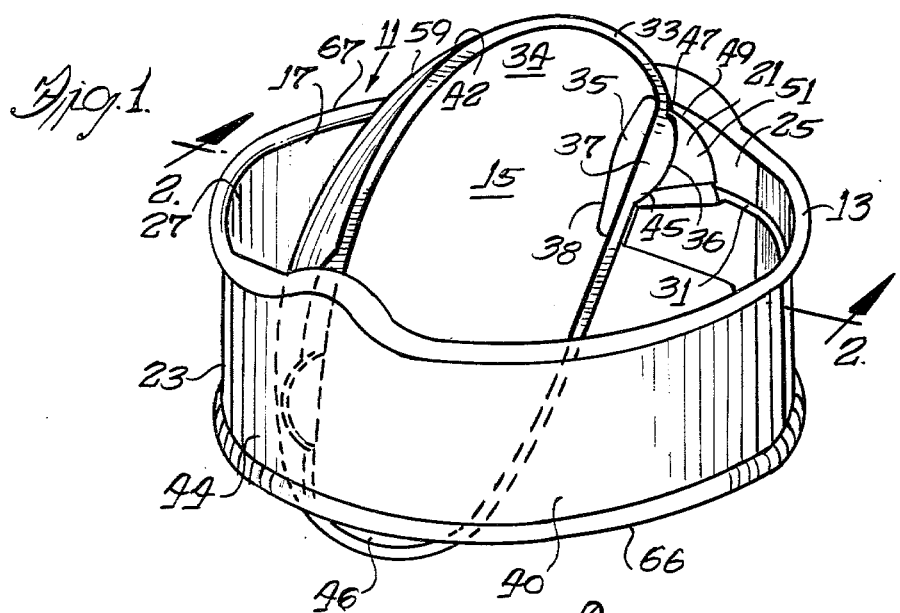
FIG. 1 is a perspective view of an occluder heart valve embodying various features of the present invention.
Figure 2:
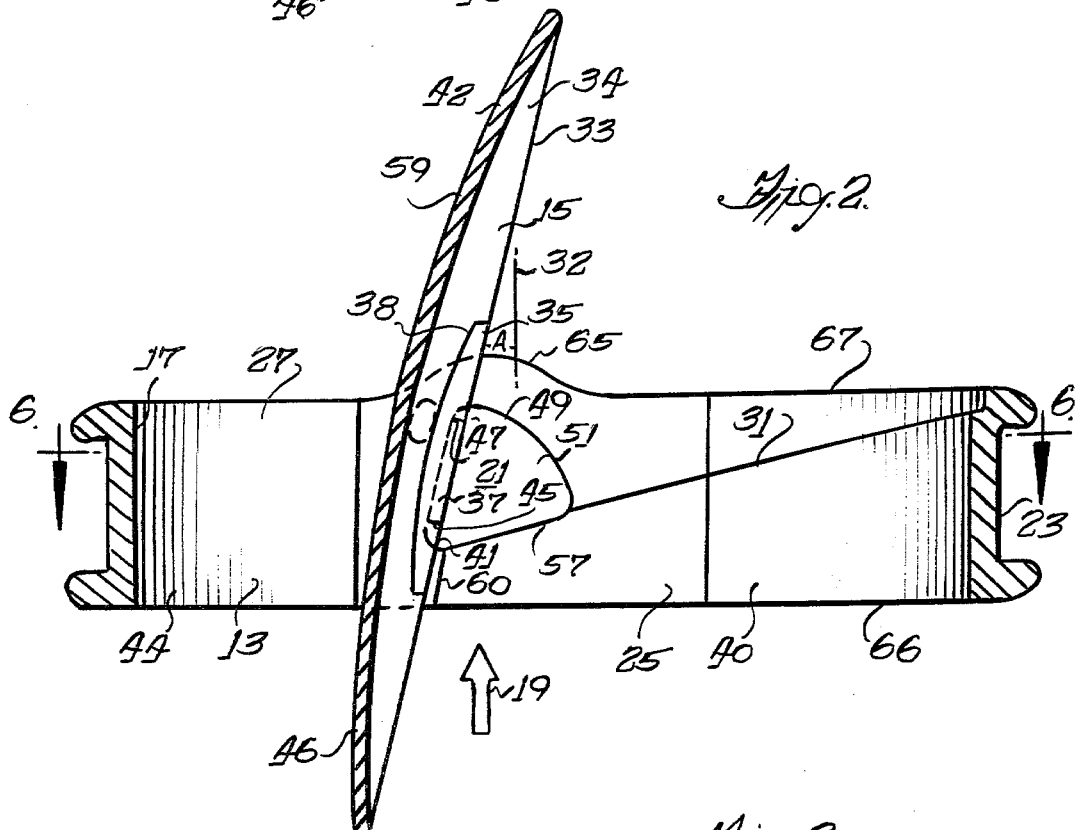
FIG. 2 is a cross-sectional view of the heart valve taken along line 2—2 of FIG. 1.

Illustrated in FIG. 1 is a heart valve 11 which has an annular valve body or housing 13 that carries a pivoting occluder or valve member 15 which hemodynamically opens and closes to control the flow of blood through a central passageway 17 in the direction of the arrow 19 (FIG. 2). The occluder 15 is mounted for rotation about an eccentric pivot axis in a pair of opposed depressions 21 formed in the interior wall of the annular valve body 13. The valve 11 can operate in any orientation and is not significantly affected by gravity, however, for ease of explanation, the valve 11 is shown and described with the annular valve body 13 being disposed horizontally.

The valve body 13 is formed with a peripheral groove 23 about its exterior surface that accommodates a suturing ring (not shown) which may be of any of the various types already well-known in the art. The suturing ring facilitates the sewing or suturing of the heart valve 11 to the heart tissue.

The passageway 17 through the valve body 13 is generally circular in cross section. However, the depressions 21 are formed in planar sections 25 of the interior wall 27 which cut parallel chords across the circular passageway 17. A lip 31 also extends inward to provide a seat for the occluder, and in these respects the passageway 17 deviates slightly from being perfectly circular in cross section. As best seen in FIG. 6, the horizontal length of the planar sections 25 of the interior wall 27 of the valve body 13 is less than about a third the length of the passageway diameter, and at the most restricting point, i.e. the center of the planar sections, the passageway 17 is constricted not more than about six percent of the diameter.

The occluder 15 is generally in the shape of a concave-convex dish with a generally elliptical peripheral rim 33. The concave-convex shape of the occluder 15, in which the apex of the upstream concave side 34 is recessed from the rim 33 between about 3 and about 8 percent of the length of the diameter of the passageway 17, gives the occluder additional strength and rigidity so that the occluder will not deform easily and be inadvertently popped out of the body 13 during surgical insertion into the heart. The elliptical shape of the rim 33 is proportioned to close off the generally circular passageway 17 with the plane of the rim offset from a plane perpendicular to the centerline 32 (FIG. 2) of the valve 11 when it seats therein. That is, the elliptical shape is that formed by a plane cutting a right circular cylinder at the angle at which the occluder 15 seats in the body 13. In some cases, e.g., where it is desirable to minimize the thickness of the valve 11, a generally circular occluder may be provided which seats in the valve body perpendicular to the centerline. The elliptical shape of the occluder rim 33 is interrupted by opposed parallel flat sides 35 which are perpendicular to the pivot axis and which are spaced apart just slightly less than the distance between the planar sections 25 of the interior wall 27 to permit free rotation of the occluder 15. The flat sides 35 of the occluder 15 are disposed perpendicular to the plane of the rim 33 and extend from the rim to a curved junction 38 with the concave-convex portion.

An ear 37, generally in the shape of a segment of a thin cylinder, protrudes from each flat side 35 of the occluder 15 and into the corresponding depression 21 to pivotably mount the occluder in the valve body 13. The ears 37 are generally coplanar with the occluder rim 33 and have arcuate edges 36 which are rounded between their flat surfaces for smooth guidance within the depressions 21 and to eliminate sharp edges which could result in wear at the pivot points.

The complementary depressions 21 in the planar sections have a periphery which is generally pie-shaped, i.e., a circular sector with the vertices directed in the upstream direction and away from the centerline 32 of the body 13. The upstream ends 45 of the ears, distal to the centerline, rotate relative to the corresponding vertices 41 of the depressions 21 to define therewith a pivot axis which is parallel to the minor elliptical axis of the occluder 15. The eccentric pivot axis divides the body 13 and occluder 15 into major portions 40 and 42 to the right of the vertices 41 in reference to FIG. 2 and minor portions 44 and 46 to the left of the vertices. The downstream ends 47 of the ears 37 are guided by the arcuate edges 49 as the occluder 15 pivots between its open and closed positions. The vertex 41 (FIG. 2) of each depression 21 is rounded for smooth rotation of the corresponding ear 37 relative thereto.

The back wall 51 of each depression 21 is concave between the vertex 41 and the arcuate edge 49 to generally match the arcuate edges 36 of the ears 37. As the flat sides 35 of the occluder 15 are spaced slightly from the planar sections 25 of the interior wall 27, some lateral movement of the occluder within the body 13 will occur. So that the thrust of lateral movement is borne by the planar sections 25 and the flat sides 35 rather than by the more vulnerable ears 37 and the depressions 21, the concave radius of curvature of the depressions 21 is preferably between about 5% and about 20% greater than the radius of curvature of the arcuate edges 36 of the ears leaving a greater average spacing between the ears and the back walls 51 than the spacing between the flat sides 35 and the planar sections 25. Thus the planar sections 25 serve as the lateral guides for the occluder 15 by guiding the flat sides 25 therebetween. The shallow, broad configuration of the pie-shaped depressions 21 provides for good washing of the depressions by blood. The loose fit of the ears 37 within the depressions 21 allows an acceptable amount of back flow of blood around the ears when the valve 11 is closed to continually wash the depressions and prevent stagnation and clotting therein.

The occluder 15 is stopped in its closed position against the lip 31 which projects into the passageway 17 from the interior wall of the major portion 40 of the valve body 13. Between the arcuate edges 49 of the depressions 21, the downstream surface of the lip 31 is matched to the shape of the leaflet rim 33 which seats thereagainst in its closed position at an angle B (FIG. 3) to the centerline of between about 75° to about 90° and preferably between about 75° and about 85°. The upstream straight edges 57 of the depressions 21 are generally parallel to the plane of the closed occluder rim 33 but spaced slightly upstream therefrom so that the force of closing is borne by about 50 percent of the occluder rim and by the lip 31 and is thereby unloaded from the ears 37 and the depressions so that problems due to wear on the pivots are substantially eliminated. Below the depressions 21, the lip 31 dips down slightly and is flush with the upstream straight edges 57 of the depressions. The lip 31 ends short of the vertices 41 of the depressions 21, and the back edges 60 of the lip are generally parallel to, but spaced from, the rim 33 of the occluder 15 in its open position (FIG. 2). In addition to unloading force on the ears 37, the spacing of the upstream edge 57 from the rim 33 of the closed occluder 15 insures continual washing of blood in the problematic area along the upstream edge. As the periphery of the occluder 15 is proportioned to allow a small clearance between it and the interior wall 27 so that the occluder may pivot freely without binding, an acceptable amount of back flow occurs between the minor portions 44, 46 of the closed occluder and the body 13.

The distribution of closing force over the length of the seating lip 31 also permits a softer closing of the valve 11 than would be possible if the closing force were absorbed by a more limited area such as between the upstream straight edges 57 and the ears 37. The softer closing reduces blood cell crushing (hemolysis).

The abutting of the ears 37 against the downstream straight edges 55 of the depressions 21 stops pivoting of the occluder 15 in its open position. The equalization of pressure on both sides of the occluder 15, as the occluder approaches its fully open position, reduces the force with which the ear 37 and the downstream edges 55 of the depressions 21 impact, and, hence, the stopping of the occluder in its open position results neither in significant wear on the ears 37 nor in hemolysis.

To provide a further positive stop for the occluder 15 in its open position, opposed protrusions 56 (FIG. 4) extend inward from the planar sections 25 at a position spaced from the upper ends of the downstream straight edges 55 of the corresponding depressions 21 to abut the downstream convex surface 59 of the occluder 15. The protrusions 56 furthermore eliminate any chance that the occluder 15 will pop from the body 13 in its open position.

Figure 3:
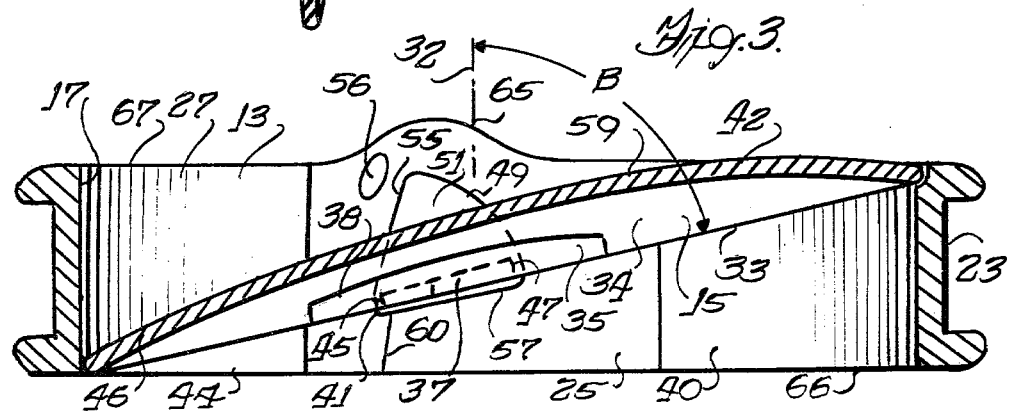
FIG. 3 is a cross-sectional view similar to that of FIG. 2 but showing the occluder in the closed position.

As best seen in FIGS. 2 and 3, the annular valve body 13 has a very low profile which is considered an important feature of a heart valve. The lower rim 66 of the body 13 is flat, and only a pair of reinforcing protrusions 65 extend above the depressions 21 to interrupt the plane of the upper rim 67. The low profile facilitates machining of the valve components and facilitates placement of the valve 11 in the heart of the recipient. Because the valve body 13 is the area of greatest restriction, the low profile keeps pressure drop through the valve 11 to a minimum.

For a valve 11 in the aortic position, in the pumping stroke of the heart as the respective ventricle contracts, blood is pushed against the entire concave upstream surface 34 of the occluder 15. The greater force against the occluder 15 is naturally on its major portion 42 resulting in the major portion pivoting downstream to open the valve. As the occluder 15 in its closed position is angled so that its major portion 42 is already pointed in the downstream direction, blood initially contacting its minor portion 46 is deflected toward its major portion, thereby facilitating opening of the valve 11.

While it is desirable for unobstructed blood flow that the occluder 15 open until the plane of its rim 33 is close to parallel with the centerline 32, it is necessary that the plane of the rim in the open position be angled somewhat from the centerline so that when the respective ventricle relaxes to draw more blood into the chamber from the atrium, the backflow of blood from the aorta exerts a drag force against the major portion 42 of the occluder 15 which is angled into the stream of backflow. Thus the downstream edges 55 of the depressions 21, against which the ears stop in the open position of the occluder 15, are angled from the centerline 32 an angle A (FIG. 2) of between about 5° and about 20° with the centerline to determine the angle which the plane of the rim 33 of the open occluder makes with the centerline. Once the occluder 15 begins to close, the angle between the plane of the rim 33 and the centerline 32 increases, thereby increasing the drag on the occluder, and the occluder rapidly snaps shuts with a minimum of blood regurgitation. Since, in most cases, the plane of the rim 33 in the closed position is offset from a plane perpendicular to the centerline 32, the total anglular rotation of the occluder 15 between the fully closed and the fully open position is typically only about 65°, and the short angle of pivoting contributes to the quick opening and closing of the valve 11.

The valve body 13 and the occluder 15 are made of suitable material that is biocompatible and nonthrombogenic and that will take the wear to which they will be subjected during countless openings and closings of the occluder. Preferably, the valve body 13 is made from isotropic polycrystalline graphite, such as that sold under the trademark POCO, which has been suitably coated with pyrolytic carbon, such as that marketed under the trademark PYROLITE, which gives excellent biocompatibility and wear-resistance. Alternatively, the valve body 13 may be made entirely from pyrolytic carbon. The occluder 15 is thin, and preferably has a thickness of less than about 5% of the passageway diameter, so as not to materially obstruct blood flow when in its open position, and light so as to respond quickly to blood pressure changes, and it is preferably formed as a unitary piece of pyrolytic carbon.

As the body 13 and the occluder 15 are manufactured separately, and as the width of the occluder through the midpoint of the ears 37 is necessarily greater than the distance between the planar sections 25, the body and/or the occluder must be sufficiently resiliently deformable so that the ears may be snapped into the depressions 21. Both the body 13 and the occluder 15, however, should be sufficiently resistant to deformation so that there is substantially no likelihood that the occluder will be accidentally snapped out of the body during insertion into the heart. The concave-convex shape of the thin pyrolytic carbon occluder 15 provides sufficient strength to resist deformation during insertion into the heart.

One example of a heart valve 11 designed for aortic location may have an outside diameter of about 24 mm. and an interior diameter of about 21 mm. The faces of the flat chordal sections 25 are spaced about 20 mm. apart. The distance from the vertex 41 to the arcuate edge 49 of each depression 21 may be about 5 mm., and the concave radius of curvature of the back wall 51 between the vertex 41 and the arcuate edge 49 is about 2.6 mm. resulting in a maximum depression depth of 2 mm. The flat sides 35 of the occluder 15 are about 19 mm. apart, and the remainder of the occluder periphery is proportioned to leave about a 0.5 mm. clearance between the closed occluder and the interior wall 27. The arcuate edges 36 of the ears 37 each have a 2.3 mm. peripheral radius of curvature and extend 1.8 mm. outward from the flat sides 35. The seating lip 31 is about 1 mm. wide. The vertical height of the body 13 is about 5 mm. and the reinforcing protrusions 65 extend about 2 mm. upward therefrom.

While the invention has been described in terms of a preferred embodiment, modifications obvious to one skilled in the art may be made without departing from the scope of the present invention. For example, instead of having a cylindrical shape, the ears could have a generally rectangular shape and locate between parallel flat back walls of corresponding pie-shaped depressions.

Various features of the invention are set forth in the following claims.

What is claimed is:

1. A heart valve prosthesis comprising:
    an annular valve body having a generally circular central passageway therethrough with a pair of central opposed planar sections designed to permit the flow of blood therethrough in a predetermined downstream direction and having a pair of opposed pie-shaped depressions recessed in said planar sections and each having an upstream vertex distal to the centerline of said body, an upstream straight edge, a downstream straight edge and an arcuate edge connecting said straight edges;
    a single occluder having a pair of ears which extend outward from a pair of flat sides into said depressions whereby said occluder is mounted for substantially pivotal movement along an eccentric pivot axis defined by the rotation of said ears relative to said vertices of said depressions, which pivot axis divides said occluder and said valve body into major and minor portions, said single occluder being pivotable between a closed position to block blood flow through said central passageway, and an open position allowing blood flow therethrough in said predetermined downstream direction;
    said occluder having a concave-convex configuration and a generally elliptical periphery and being mounted in said annular valve body with its pivotal axis parallel to its minor elliptical axis and with the concave surface facing upstream;
    and a lip projecting into said passageway from said major portion of said valve body having a downstream-facing surface along which said occluder seats in said closed position and which is oriented at an angle of between about 75° and about 85° to the centerline of said valve body.

2. A prosthesis according to claim 1 wherein said occluder is disposed in said open position at an angle of between about 5° to about 20° with the centerline of said body.

3. A prosthesis according to claim 1 wherein the vertex of said concave side of said leaflet is recessed from its periphery a distance of between about 3 percent and about 8 percent of the length of the diameter of said passageway.

4. A prosthesis according to claim 1 wherein the thickness of said occluder is less than about 5 percent of the length of the diameter of said passageway.

5. A prosthesis according to claim 1 wherein said upstream straight edges of said depressions are disposed upstream of said occluder in said closed position.

6. A heart valve in accordance with claim 1 wherein said ears have arcuate outer edges having a radius of curvature slightly less than the corresponding radius of curvature of the concave rear walls of said depressions.

7. A heart valve in accordance with claim 1 wherein rounded protrusions project from said planar sections at locations spaced from said downstream straight edges of said depressions, which protrusions are engaged by the downstream convex surface of said occluder to determine the open position thereof.

* * * * *